(12) United States Patent
Epp et al.

(10) Patent No.: US 8,357,633 B2
(45) Date of Patent: *Jan. 22, 2013

(54) 2-(2-FLUORO-SUBSTITUTED PHENYL)-6-AMINO-5-CHLORO-4-PYRIMIDINECARBOXYLATES AND THEIR USE AS HERBICIDES

(75) Inventors: Jeffrey B. Epp, Noblesville, IN (US); William C. Lo, Fishers, IN (US); Paul R. Schmitzer, Indianapolis, IN (US); Carla N. Yerkes, Crawfordsville, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 183 days.

This patent is subject to a terminal disclaimer.

(21) Appl. No.: 12/688,145

(22) Filed: Jan. 15, 2010

(65) Prior Publication Data

US 2010/0120621 A1 May 13, 2010

Related U.S. Application Data

(63) Continuation of application No. 12/182,675, filed on Jul. 30, 2008, now Pat. No. 7,915,200.

(60) Provisional application No. 60/964,504, filed on Aug. 31, 2007, provisional application No. 61/124,606, filed on Apr. 18, 2008.

(51) Int. Cl.
*A01N 43/54* (2006.01)
(52) U.S. Cl. ........................................ 504/239; 544/329
(58) Field of Classification Search .................. 504/239; 544/329
See application file for complete search history.

(56) References Cited

U.S. PATENT DOCUMENTS

| 7,300,907 | B2 | 11/2007 | Epp et al. | |
| 7,915,200 | B2 * | 3/2011 | Epp et al. | 504/239 |

FOREIGN PATENT DOCUMENTS

| WO | WO2005/063721 A1 | 7/2005 |
| WO | WO2007/082076 A1 | 7/2007 |
| WO | 2008/071578 | 6/2008 |

* cited by examiner

*Primary Examiner* — Deepak Rao
(74) *Attorney, Agent, or Firm* — Robert Chang; Craig E. Mixan

(57) ABSTRACT

2-(2-Fluoro-substituted phenyl)-6-amino-5-chloro-4-pyrimidine carboxylic acid and its derivatives are potent herbicides demonstrating a broad spectrum of weed control.

14 Claims, No Drawings

2-(2-FLUORO-SUBSTITUTED PHENYL)-6-AMINO-5-CHLORO-4-PYRIMIDINECARBOXYLATES AND THEIR USE AS HERBICIDES

This application is a continuation of application Ser. No. 12/182,675, filed on Jul. 30, 2008 now U.S. Pat. No. 7,915,200, and claims benefit of U.S. Provisional Applications Ser. Nos. 60/964,504 and 61/124,606 filed respectively on Aug. 31, 2007 and Apr. 8, 2008.

BACKGROUND OF THE INVENTION

This invention relates to 2-(2-fluoro-substituted phenyl)-6-amino-5-chloro-4-pyrimidinecarboxylic acids and their derivatives and to the use of these compounds as herbicides.

A number of pyrimidinecarboxylic acids and their pesticidal properties have been described in the art. WO 2005/063721 A1, WO 2007/082076 A1 and U.S. Pat. No. 7,300,907 (B2) disclose certain 2-substituted-6-amino-4-pyrimidinecarboxylic acids and their derivatives and their use as herbicides. It has now been discovered that certain particular subclasses of the compounds disclosed in these references have greatly improved herbicidal activity and selectivity.

SUMMARY OF THE INVENTION

It has now been found that 2-(2-fluoro-substituted phenyl)-6-amino-5-chloro-4-pyrimidinecarboxylic acids and their derivatives are superior herbicides with a broad spectrum of weed control against broadleaf weeds as well as grass and sedge weeds and with excellent crop selectivity at low use rates. The compounds further possess excellent toxicological or environmental profiles.

The invention includes compounds of Formula I:

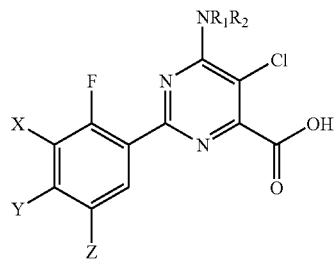

I wherein
X represents H or halogen;
Y represents halogen, $C_1$-$C_4$ alkyl or $C_1$-$C_4$ haloalkyl;
Z represents H or halogen, with the proviso that when Z is halogen then X represents H; and
$R_1$ and $R_2$ independently represent H, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated ring;
and agriculturally acceptable derivatives of the carboxylic acid group.

Preferred compounds of formula (I) include those in which Y represents halogen, most preferably Cl.

The invention includes herbicidal compositions comprising an herbicidally effective amount of a compound of Formula I and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

The herbicidal compounds of the present invention are derivatives of 2-(2-fluoro-substituted phenyl)-6-amino-5-chloro-4-pyrimidinecarboxylic acid of formula:

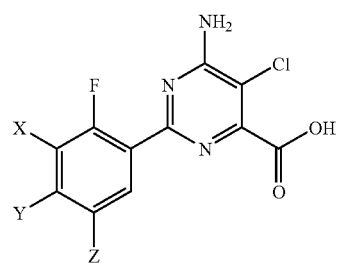

wherein
X represents H or halogen;
Y represents halogen, $C_1$-$C_4$ alkyl or $C_1$-$C_4$ haloalkyl; and
Z represents H or halogen, with the proviso that when Z is halogen then X represents H.

The amino group at the 6-position of the pyrimidine ring can be unsubstituted or substituted with one or more $C_1$-$C_6$ alkyl, $C_3$-$C_6$ alkenyl, $C_3$-$C_6$ alkynyl, hydroxy, $C_1$-$C_6$ alkoxy or amino substituents. The amino group can be further derivatized as an amide, a carbamate, a urea, a sulfonamide, a silylamine or a phosphoramidate. Such derivatives are capable of breaking down into the amine. An unsubstituted amino group or one substituted with one or two alkyl substituents is preferred.

The carboxylic acids of Formula I are believed to be the compounds that actually kill or control undesirable vegetation and are typically preferred. Analogs of these compounds in which the acid group of the pyrimidine carboxylic acid is derivatized to form a related substituent that can be transformed within plants or the environment to an acid group possess essentially the same herbicidal effect and are within the scope of the invention. Therefore, an "agriculturally acceptable derivative", when used to describe the carboxylic acid functionality at the 4-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 2-(2-fluoro-substituted phenyl)-6-amino-5-chloro-4-pyrimidinecarboxylic acid, and (b) is or can be hydrolyzed, oxidized or metabolized in plants or soil to the 2-(2-fluoro-substituted phenyl)-6-amino-5-chloro-4-pyrimidinecarboxylic acid that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 6-position, is defined as any salt, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 2-(2-fluoro-substituted phenyl)-6-amino-5-chloro-4-pyrimidinecarboxylic acid, and (b) is or can be hydrolyzed in plants or soil to a free amine of Formula I. N-Oxides which are also capable of breaking into the parent pyrimidine of Formula I are also covered by the scope of this invention.

Suitable salts include those derived from alkali or alkaline earth metals and those derived from ammonia and amines. Preferred cations include sodium, potassium, magnesium, and aminium cations of the formula:

$$R_3R_4R_5NH^+$$

wherein $R_3$, $R_4$ and $R_5$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_3$, $R_4$, and $R_5$ are sterically compatible. Additionally, any two of $R_3$, $R_4$, and $R_5$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, ethanol, n-propanol, iso-propanol, butanol, 2-ethylhexanol, butoxyethanol, methoxypropanol, allyl alcohol, propargyl alcohol, benzyl alcohol or cyclohexanol. Esters can be prepared by coupling of the 2-(2-fluoro-substituted phenyl)-6-amino-5-chloro-4-pyrimidine-carboxylic acid with the alcohol using any number of suitable activating agents such as those used for peptide couplings such as dicyclohexylcarbodiimide (DCC) or carbonyl diimidazole (CDI), by reacting the corresponding acid chloride of 2-(2-fluoro-substituted phenyl)-6-amino-5-chloro-4-pyrimidinecarboxylic acid with an appropriate alcohol, by reacting the 2-(2-fluoro-substituted phenyl)-6-amino-5-chloro-4-pyrimidinecarboxylic acid with an appropriate alcohol in the presence of an acid catalyst or by transesterification. Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the 2-(2-fluoro-substituted phenyl)-6-amino-5-chloro-4-pyrimidinecarboxylic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. The terms "alkenyl" and "alkynyl" are intended to include one or more unsaturated bonds.

Unless specifically limited otherwise, the term "halogen" including derivative terms such as "halo" refers to fluorine, chlorine, bromine, and iodine.

The compounds of Formula I can be made using well-known chemical procedures. Many procedural details for making compounds of Formula I can be found in the following patent applications: WO 2007/082076 A1, WO 2005/063721 A1 and U.S. Pat. No. 7,300,907 (B2). Intermediates not specifically mentioned in the above patent applications are either commercially available, can be made by routes disclosed in the chemical literature, or can be readily synthesized from commercial starting materials utilizing standard procedures.

As shown in Scheme 1, the 2-(2-fluoro-substituted phenyl)-6-amino-5-chloro-4-pyrimidinecarboxylic acid esters of Formula I can be prepared by reaction of an appropriately substituted pyrimidine of Formula II with a facile leaving group L, and an organometallic compound of type III in an inert solvent in the presence of a transition metal catalyst.

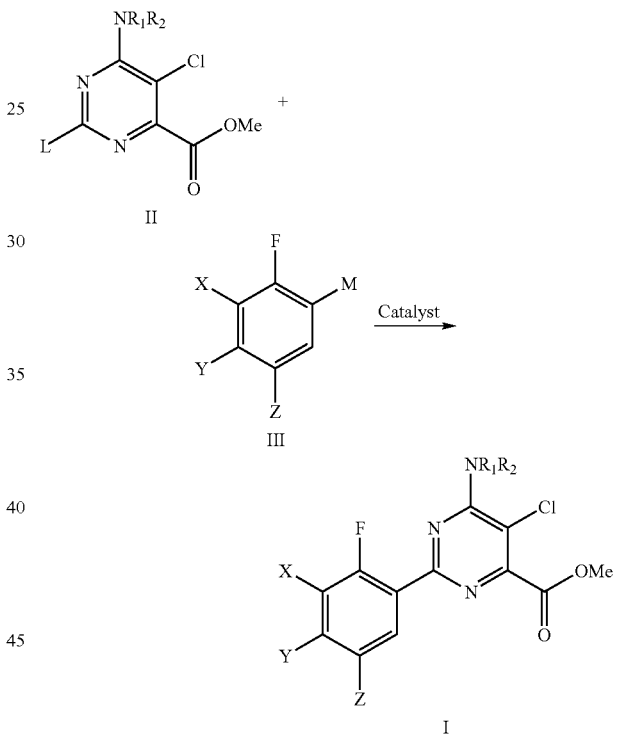

In this case L can be chlorine or bromine; M can be tri-($C_1$-$C_4$ alkyl)tin or B(OR$_6$)(OR$_7$), where $R_6$ and $R_7$ are independently of one another, hydrogen, $C_1$-$C_6$ alkyl, or when taken together form an ethylene or propylene group; and "Catalyst" can be a transition metal catalyst, in particular a palladium catalyst such as bis(triphenylphosphine)palladium(II) dichloride. The method of Scheme 1 is illustrated in Example 6.

The coupling of II+III may, where appropriate, be followed by reactions on either ring to obtain further derivatives of the compounds of Formula I.

Alternatively, as shown in Scheme 2, the 2-(2-fluoro-substituted phenyl)-6-amino-5-chloro-4-pyrimidinecarboxylic acid esters of Formula I can be prepared by reaction of compounds of formula IV with a positive chlorine source such as N-chlorosuccinimide (NCS) in an inert aprotic solvent such as acetonitrile. The method of Scheme 2 is illustrated in Example 13.

Scheme 2

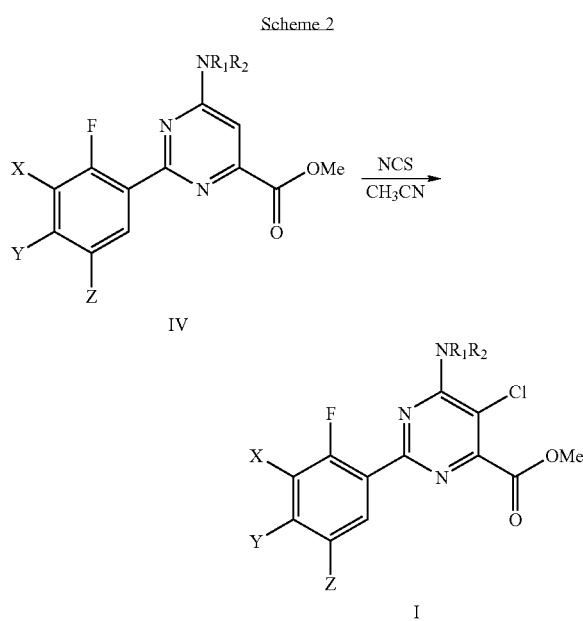

As shown in Scheme 3, appropriately substituted pyrimidines of Formula IV can be prepared by oxidation of pyrimidines of Formula V with a peracid such as m-chloroperbenzoic acid (MCPBA) in an inert solvent such as chloroform; followed by reaction with a cyanide salt such as potassium cyanide in a polar aprotic solvent such as dimethyl sulfoxide (DMSO); followed by conversion to an alkyl ester by heating in an alcohol solvent in the presence of HCl. The synthesis sequence of Scheme 3 is illustrated in Example 12.

Scheme 3

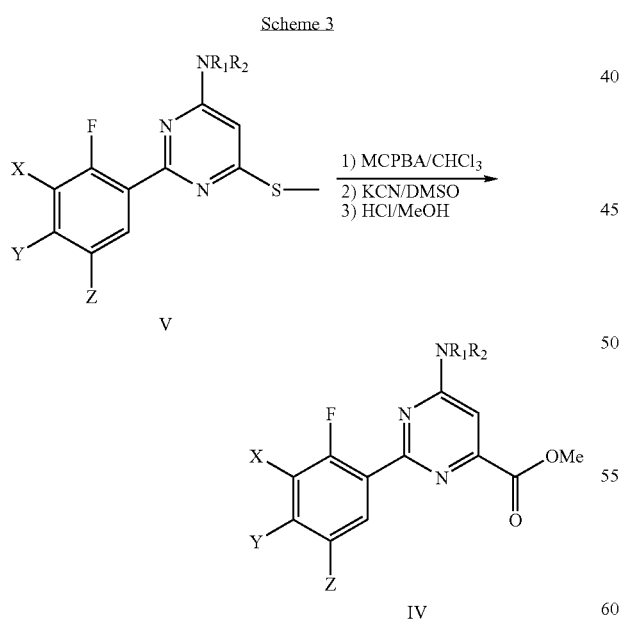

As shown in Scheme 4, appropriately substituted pyrimidines of Formula V can be prepared from compounds of Formula VI by a thermal decarboxylation reaction in the presence of an acid such as p-toluenesulfonic acid in an inert solvent such as Dowtherm A; followed by a chlorination reaction with a reagent such as phosphorous oxychloride; followed by reaction with an amine of Formula VII. The synthesis sequence of Scheme 4 is illustrated in Example 11.

Scheme 4

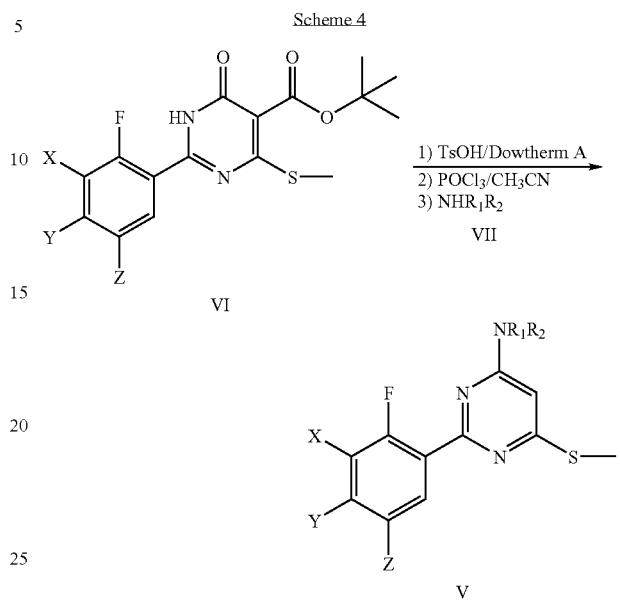

As shown in Scheme 5, appropriately substituted compounds of Formula VI can be prepared by reaction of compounds of Formula VIII with compounds of Formula IX utilizing a strong base such as sodium hydride in a polar aprotic solvent such as DMF; followed by neutralization and a period of heating in an alcoholic solvent. The synthesis sequence of Scheme 5 is illustrated in Example 10.

Scheme 5

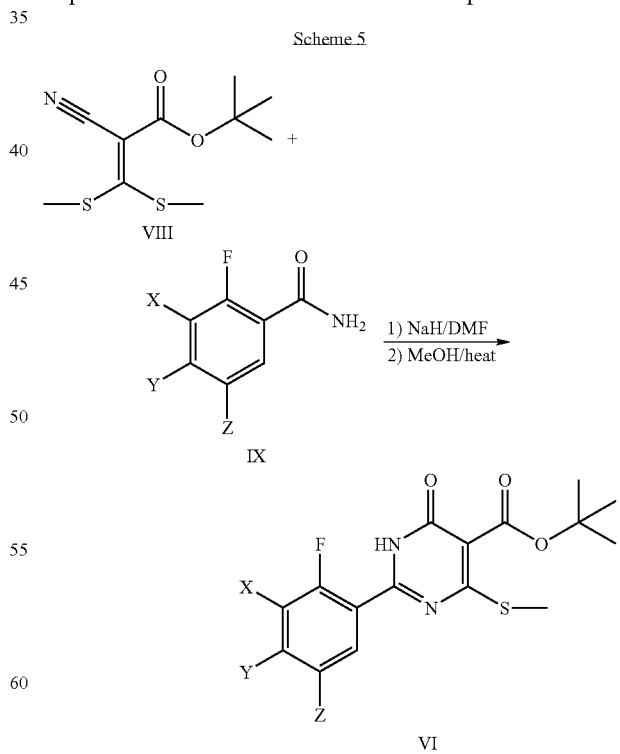

As shown in Scheme 6, compounds of Formula VIII can be prepared by reaction of compounds of Formula X with carbon disulfide and iodomethane. The method of Scheme 6 is illustrated in Example 9.

Scheme 6

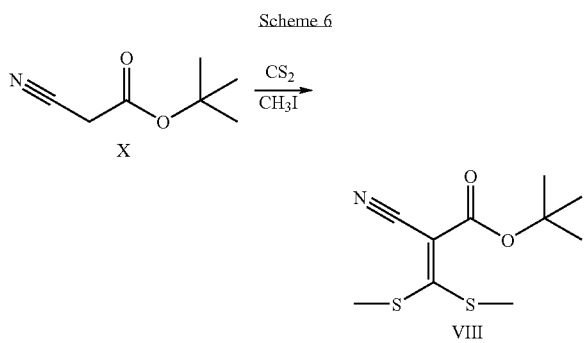

It is recognized that some reagents and reaction conditions disclosed herein or in the chemical literature for preparing compounds of Formula I may not be compatible with certain functionalities present in the intermediates. In these instances, the incorporation of protection/deprotection sequences or functional group interconversions into the synthesis will aid in obtaining the desired products. The use and choice of the protection groups will be apparent to one skilled in chemical synthesis.

One skilled in the art will recognize that, in some cases, after the introduction of a given reagent as disclosed herein or in the chemical literature, it may be necessary to perform additional routine synthetic steps not described in detail to complete the synthesis of compounds of Formula I. One skilled in the art will also recognize that it may be necessary to perform a combination of the steps disclosed herein or in the chemical literature in an order other than that implied by the particular sequences presented to prepare the compounds of Formula I.

Finally, one skilled in the art will also recognize that compounds of Formula I and the intermediates described herein or in the chemical literature can be subjected to various electrophilic, nucleophilic, radical, organometallic, oxidation, and reduction reactions to add substituents or modify existing substituents.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, turf, roadsides and rights of way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds postemergence. It is further usually preferred to use the compounds to control a wide spectrum of woody plants, broadleaf and grass weeds, and sedges. Use of the compounds to control undesirable vegetation in established crops is especially indicated. While each of the 2-(2-fluoro-substituted phenyl)-6-amino-5-chloro-4-pyrimidinecarboxylate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 1,000 g/Ha are generally employed in postemergence operations; for preemergence applications, rates of about 10 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, diallate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyrdiethyl, MG 191, MON 4660, naphthalic anhydride (NA), oxabetrinil, R29148 and N-phenyl-sulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 2-(2-fluoro-substituted phenyl)-6-amino-5-chloro-4-pyrimidinecarboxylate compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzene-sulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

1. Preparation of 4,5-Dichloro-2-fluorophenylamine

Tin (II) chloride dehydrate (27.0 g, 119.6 mmol) was dissolved in ethanol and 1,2-dichloro-4-fluoro-5-nitrobenzene (5.0 g, 23.8 mmol) was added dropwise. Temperature rose to near reflux during the addition and was complete upon cooling. The reaction mixture was carefully added to saturated aqueous sodium bicarbonate and then extracted with ethyl acetate. The organic phase was washed several more times with water, dried, filtered and concentrated to give the title compound as a yellow solid: $^1$H NMR (CDCl$_3$): δ 7.17 (d, 1H), 6.84 (d, 1H), 3.78 (br s, 2H).

Another compound prepared by the procedure of Example 1 is:
2,5-Difluoro-4-methylphenylamine: $^1$H NMR (CDCl$_3$): δ 6.78 (dd, 1H), 6.42 (dd, 1H), 3.63 (br s, 2H), 2.15 (d, 3H).

2. Preparation of 1-Bromo-4,5-dichloro-2-fluorobenzene

Anhydrous copper (II) bromide (1.5 g, 6.7 mmol) and t-butyl nitrite (0.87 g, 8.4 mmol) were combined in anhydrous acetonitrile (15 mL). The resulting mixture was heated to 65° C. and a solution of 4,5-dichloro-2-fluoro-phenylamine (1.0 g, 5.59 mmol) in anhydrous acetonitrile (2 mL) was added dropwise (vigorous gas evolution was noted). After allowing to cool to ambient temperature, the reaction mixture was added to 2N HCl and extracted with ether twice. The organic extracts were then combined, washed with 2N HCl, washed with saturated sodium bicarbonate, dried, concentrated and chromatographed to give the title compound as an orange solid (1.0 g, 73.5% yield): $^1$H NMR (CDCl$_3$): δ 7.67 (d, 1H), 7.27 (d, 1H).

Another compound prepared by the procedure of Example 2 is:
1-Bromo-2,5-difluoro-4-methylbenzene: $^1$H NMR (CDCl$_3$): δ 7.1 (dd, 1H), 6.94 (dd, 1H), 2.22 (d, 3H).

3. Preparation of 2-(4,5-Dichloro-2-fluorophenyl)-4,4,5,5-tetramethyl-[1,3,2]dioxaborolane 1-Bromo-4,5-dichloro-2-fluorobenzene (1.0 g, 4.11 mmol) was dissolved in tetrahydrofuran (THF; 20 mL) and cooled to −10° C. A 2.0M solution of isopropylmagnesium chloride (2.3 mL, 4.6 mmol) in THF was added dropwise via a syringe. The reaction mixture was stirred at −10° C. for 1 hour, allowed to warm toward 0° C. for 1 hour, then cooled to −10° C. again. A solution of 2-isopropoxy-4,4,5,5-tetramethyl[1,3,2]dioxaborolane (0.85 g, 4.56 mmol) in THF (1.0 mL) was then added dropwise and the reaction was allowed to warm to ambient temperature. The reaction mixture was then added to diethyl ether and extracted with 1N sodium hydroxide. The aqueous phases were combined, acidified to pH 3 with concentrated HCl, and extracted with dichloromethane twice. The organic phases were combined, dried, filtered and concentrated to give the title compound (0.85 g, 71% yield) that was used without further purification: $^1$H NMR (CDCl$_3$): δ 7.73 (d, 1H), 7.12 (d, 1H), 1.3 (s, 12H).

Another compound prepared by the procedure of Example 3 is:
2-(2,5-Difluoro-4-methylphenyl)-4,4,5,5-tetramethyl[1,3,2]dioxaborolane: $^1$H NMR (CDCl$_3$): δ 7.32 (dd, 1H), 6.83 (dd, 1H), 1.34 (s, 12H).

4. Preparation of 2-(4-Chloro-2,3-difluorophenyl)-4,4,5,5-tetramethyl-[1,3,2]dioxaborolane A 2.5 M solution of n-butyllithium (2.69 ml, 6.73 mmol) in hexanes was added dropwise to a solution of 1-chloro-2,3-difluorobenzene (1 g, 6.73 mmol) in THF (25 mL) cooled to −78° C. After 45 minutes at −78° C., 2-isopropoxy-4,4,5,5-tetramethyl[1,3,2]dioxaborolane (1.253 g, 6.73 mmol) was added dropwise after which the reaction mixture was allowed to warm to ambient temperature. The reaction mixture was diluted with water and ethyl acetate and the organic phase was extracted twice with water. The aqueous extracts were combined and acidified with 12N HCl to pH 3. The product was then extracted with ethyl acetate. The organic phase was dried and concentrated under vacuum to yield the title compound as an oil product (0.93 g, 50% yield): $^1$H NMR (CDCl$_3$): δ 7.42 (m, 1H), 7.17 (m, 1H), 1.37 (s, 12H).

5. Preparation of 2-(2,3-Difluoro-4-methylphenyl)-4,4,5,5-tetramethyl-[1,3,2]dioxaborolane A 2.5 M solution of n-butyllithium (3.4 mL, 8.5 mmol) was added to a stirred solution of diisopropylamine (1.2 mL, 8.5 mmol) in THF (25 mL) at −20° C. The resulting solution was stirred at −20° C. for 10 minutes, then cooled to −78° C. A solution of 1,2-difluoro-3-methylbenzene (1.0 g, 7.8 mmol) in THF was added dropwise and stirred at −78° C. for 2 h. 2-Isopropoxy-4,4,5,5-tetramethyl[1,3,2]dioxaborolane (1.6 g, 8.6 mmol) in THF was then added and the brown solution was slowly warmed to 23° C. over 16 hours. The reaction mixture was then added to ether and extracted with water and with 0.1N sodium hydroxide. The combined aqueous extracts were acidified with concentrated HCl then extracted with dichloromethane. The organic phase was dried and concentrated to give the title compound (1.0 g, 50% yield): $^1$H NMR (CDCl$_3$): δ 7.32 (m, 1H), 6.92 (m, 1H), 2.31 (s, 3H), 1.32 (s, 12H).

Another compound prepared by the procedure of Example 5 is:
2-(2,3-Difluoro-4-trifluoromethylphenyl)-4,4,5,5-tetramethyl[1,3,2]-dioxaborolane: $^1$H NMR (CDCl$_3$): δ 7.55 (m, 1H), 7.33 (m, 1H) 1.35 (s, 12H).

6. Preparation of 6-Amino-5-chloro-2-(4-chloro-2-fluorophenyl)pyrimidine-4-carboxylic acid methyl ester (Compound 1)

6-Amino-2,5-dichloropyrimidine-4-carboxylic acid methyl ester (1.11 g, 5 mmol, see WO 2007/082076 A1 for preparation), 4-chloro-2-fluorophenylboronic acid (1.13 g, 6.5 mmol), bis(triphenylphosphine)-palladium(II) dichloride (350 mg, 0.5 mmol), and cesium fluoride (1.52 g, 10 mmol) were combined in 10 mL of 1,2-dimethoxyethane (DME) and 10 mL of water. The reaction mixture was heated in a CEM microwave at 100° C. for 15 minutes. The cooled reaction mixture was diluted with ethyl acetate, washed with water, dried and concentrated. The product was purified by column chromatography (methylene chloride/ethyl acetate gradient) then purified again by column chromatography (ethyl acetate/hexane gradient) to yield the title compound (574 mg, 40.8% yield): mp 194-196° C.; $^1$H NMR (CDCl$_3$): δ 7.96 (m, 1H), 7.2 (m, 2H), 5.64 (br s, 2H), 4.01 (s, 3H).

Other compounds prepared by the procedure of Example 6 are:
6-Amino-5-chloro-2-(4-chloro-2,3-difluorophenyl)pyrimidine-4-carboxylic acid methyl ester (Compound 2): mp 187-189° C.; $^1$H NMR (CDCl$_3$): δ 7.76 (m, 1H), 7.24 (m, 1H), 5.68 (br s, 2H) 4.02 (s, 3H).
6-Amino-5-chloro-2-(2-fluoro-4-methylphenyl)pyrimidine-4-carboxylic acid methyl ester (Compound 3): $^1$H NMR (CDCl$_3$): δ 7.86 (m, 1H), 7.01 (m, 1H), 6.95 (m, 1 h), 5.63 (br s, 2H), 4.00 (s, 3H), 2.39 (s, 3H).
6-Amino-5-chloro-2-(2,3-difluoro-4-methylphenyl)pyrimidine-4-carboxylic acid methyl ester (Compound 4): $^1$H NMR (CDCl$_3$): δ 7.62 (m, 1H), 6.97 (m, 1H), 5.62 (br s, 2H), 4.0 (s, 3H), 2.35 (s, 3H).
6-Amino-5-chloro-2-(2-fluoro-4-trifluoromethylphenyl)pyrimidine-4-carboxylic acid methyl ester (Compound 5): $^1$H NMR (DMSO-d$_6$+ few drops of D$_2$O): δ 8.03 (m, 1H), 7.78 (m, 1H), 7.7 (m, 1H), 3.9 (s, 3H).
6-Amino-5-chloro-2-(2,3-difluoro-4-trifluoromethylphenyl)pyrimidine-4-carboxylic acid methyl ester (Compound 6): $^1$H NMR (CDCl$_3$+1 drop DMSO-d$_6$): δ 7.8 (m, 1H), 7.35 (m, 1H), 6.25 (br s, 2H), 3.95 (s, 3H).
6-Amino-5-chloro-2-(2,3-difluoro-4-formylphenyl)pyrimidine-4-carboxylic acid methyl ester that was subsequently fluorinated via standard conditions to produce 6-Amino-5-chloro-2-(4-difluoromethyl-2,3-difluorophenyl)pyrimidine-4-carboxylic acid methyl ester (Compound 7), $^1$H NMR (CDCl$_3$): δ 7.78 (m, 1H), 7.33 (m, 1H), 6.86 (t, 1H), 6.3 (br s, 2H), 3.93 (s, 3H).
6-Amino-5-chloro-2-(2,5-difluoro-4-methylphenyl)pyrimidine-4-carboxylic acid methyl ester (Compound 8): $^1$H NMR (CDCl$_3$): δ 7.65 (dd, 1H), 6.97 (dd, 1H), 5.62 (br s, 2H), 4.02 (s, 3H), 2.15 (d, 3H).
6-Amino-5-chloro-2-(2-fluoro-4-formylphenyl)pyrimidine-4-carboxylic acid methyl ester that was subsequently fluorinated under standard conditions to produce 6-Amino-5- chloro-2-(4-difluoromethyl-2-fluorophenyl)pyrimidine-4-carboxylic acid methyl ester (Compound 9): ¹H NMR (CDCl₃): δ 8.05 (m, 1H), 7.36 (m, 1H), 6.65 (t, 1H), 5.63 (br s, 2H), 4.01 (s, 3H).

6-Amino-5-chloro-2-(4,5-dichloro-2-fluorophenyl)pyrimidine-4-carboxylic acid methyl ester (Compound 10): ¹H NMR (CDCl₃): δ 8.16 (d, 1H), 7.3 (d, 1H), 5.63 (br s, 2H), 4.02 (s, 3H).

7. Preparation of 6-Amino-5-chloro-2-(4-chloro-2-fluorophenyl)pyrimidine-4-carboxylic acid (Compound 11)

6-Amino-5-chloro-2-(4-chloro-2-fluorophenyl)pyrimidine-4-carboxylic acid methyl ester (400 mg, 1.26 mmol) was dissolved in 10 mL methanol and 2 mL of 2N sodium hydroxide (4 mmol) was added. The reaction mixture was stirred at room temperature for 4 hours and then acidified with a slight excess of 2N HCl. The resulting solution was concentrated and the precipitate that formed was filtered, washed with water, and dried yielding the title compound (170 mg, 44% yield): mp 194-196° C.: ¹H NMR (DMSO-d₆+ few drops of D₂O): δ 7.92 (m, 1H), 7.54 (dd, 1H), 7.42 (dd, 1H).

Other compounds prepared by the procedure of Example 7 are:

6-Amino-5-chloro-2-(4-chloro-2,3-difluorophenyl)pyrimidine-4-carboxylic acid (Compound 12): mp 209-211° C.; ¹H NMR (DMSO-d₆ and a few drops of D₂O): δ 7.79 (m, 1H), 7.55 (m, 1H).

6-Amino-5-chloro-2-(2-fluoro-4-methylphenyl)pyrimidine-4-carboxylic acid (Compound 13): ¹H NMR (DMSO-d₆+ few drops of D₂O): δ 7.78 (m, 1H), 7.13 (m, 1H), 7.1 (m, 1H), 2.37 (s, 3H).

6-Amino-5-chloro-2-(2,3-difluoro-4-methylphenyl)pyrimidine-4-carboxylic acid (Compound 14): ¹H NMR (DMSO-d₆+ few drops of D₂O): δ 7.6 (m, 1H), 7.15 (m, 1H), 2.35 (s, 3H).

6-Amino-5-chloro-2-(2-fluoro-4-trifluoromethylphenyl)pyrimidine-4-carboxylic acid (Compound 15): ¹H NMR (DMSO-d₆+ few drops of D₂O): δ 8.04 (m, 1H), 7.78 (m, 1H), 7.68 (m, 1H).

6-Amino-5-chloro-2-(2,3-difluoro-4-trifluoromethylphenyl)pyrimidine-4-carboxylic acid (Compound 16): ¹H NMR (DMSO-d₆+ few drops of D₂O): δ 7.9 (m, 1H), 7.72 (m, 1H).

6-Amino-5-chloro-2-(4,5-dichloro-2-fluorophenyl)pyrimidine-4-carboxylic acid (Compound 17): ¹H NMR (CDCl₃+ drop of DMSO-d₆): δ 8.18 (d, 1H), 7.23 (d, 1H), 6.18 (br s, 2H).

6-Amino-5-chloro-2-(2,5-difluoro-4-methylphenyl)pyrimidine-4-carboxylic acid (Compound 18): ¹H NMR (CDCl₃+ drop of DMSO-d₆): δ 7.63 (dd, 1H), 6.89 (dd, 1H), 6.18 (br s, 2H), 2.12 (d, 3H).

8. Preparation of 6-Amino-5-chloro-2-(4-chloro-2-fluorophenyl)pyrimidine-4-carboxylic acid ethyl ester (Compound 19)

A 1N solution of HCl in ethanol was generated by adding 0.565 mL of acetyl chloride dropwise to 12 mL of ethanol cooled in an ice bath. This solution was added to 200 mg of 6-amino-5-chloro-2-(4-chloro-2-fluorophenyl)-pyrimidine-4-carboxylic acid and the resulting solution was heated at 62° C. overnight. The reaction mixture was concentrated and the residue partitioned between ethyl acetate and water. The organic phase was dried and concentrated, and the product was purified by column chromatography (dichloromethane/ethyl acetate gradient). A second chromatography utilizing an amine-functionalized silica gel column (Biotage KP-NH) and an ethyl acetate/hexane gradient solvent system yielded the title compound (139 mg, 63.5% yield): mp 131-132° C.: ¹H NMR (CDCl₃): δ 7.97 (m, 1H), 7.2 (m, 2H), 5.63 (br s, 2H), 4.48 (q, 2H), 1.44 (t, 3H).

9. Preparation of 2-Cyano-3,3-bis-methylsulfanyl-acrylic acid tert-butyl ester t-Butyl cyanoacetate (4.0 g, 28 mmol) and potassium carbonate (8.6 g, 62 mmol) were combined in 60 mL dimethyl formamide (DMF) in a 3-neck flask equipped with a mechanical stirrer. To this stirred solution was added carbon disulfide (1.90 mL, 31.6 mmol) and the resulting solution was stirred for 1 hour. Iodomethane (3.70 mL, 59.4 mmol) was then added neat, the mixture was stirred for an additional 1 hour, and then added to water. This solution was extracted with ether, washed with brine, dried and filtered. The product was purified by column chromatography (ethyl acetate/hexane gradient) to give the title compound as a thick yellow oil (4.6 g, 67% yield): ¹H NMR (CDCl₃): δ 2.75 (s, 3H), 2.58 (s, 3H), 1.55 (s, 9H).

10. Preparation of 2-(4-Chloro-2,5-difluorophenyl)-4-methylsulfanyl-6-oxo-1,6-dihydropyrimidine-5-carboxylic acid tert-butyl ester 2-Cyano-3,3-bis-methylsulfanyl-acrylic acid tert-butyl ester (2.94 g, 12 mmol) and 4-chloro-2,5-difluorobenzamide (2.29 g, 12 mmol) were combined in 50 mL DMF and 60% sodium hydride (1.0 g, 25 mmol) was added in a single portion. After 1 hour, the reaction mixture was added to water and the neutralized with 2N HCl. The product was extracted with ether, dried, filtered and concentrated. The product was triturated with 30% diethyl ether/hexane to give 1.85 g of a white solid that was then heated in methanol overnight. The solid that formed when the reaction mixture cooled was filtered, rinsed with a small amount of cold methanol, and dried to give the title compound as a yellow solid (1.45 g, 31% yield for the two steps): ¹H NMR (DMSO-d₆): δ 13 (br s, 1H), 7.8-8.0 (m, 2H), 2.4 (s, 3H), 1.5 (s, 9H).

11. Preparation of 2-(4-Chloro-2,5-difluorophenyl)-6-methylsulfanyl-pyrimidin-4-ylamine 2-(4-Chloro-2,5-difluorophenyl)-4-methylsulfanyl-6-oxo-1,6-dihydropyrimidine-5-carboxylic acid tert-butyl ester (1.3 g, 3.35 mmol) and catalytic p-toluenesulfonic acid monohydrate were heated in 15 mL of Dowtherm A to a temperature of 220° C. and then to reflux for 5 minutes. The heat was then removed and the reaction flask cooled in an ice bath. A 15% diethyl ether/hexane solution was added to the reaction mixture to break up the solid that formed. This solid was filtered and washed with additional 15% diethyl ether/hexane solution and dried to give 0.92 g of an off-white solid product (90% yield). This intermediate was then combined with phosphorous oxychloride (0.54 g, 3.5 mmol) in 15 mL of acetonitrile and heated to reflux until gas evolution ceased. The reaction mixture was then allowed to cool to ambient temperature and was concentrated. The product was purified by column chromatography (diethyl ether/hexane gradient solvent system) to give 0.32 g of a white solid product (33% yield). This intermediate was then dissolved in 10 mL dimethyl sulfoxide (DMSO) and heated at 100° C. Ammonia gas was bubbled in slowly over 18 hours. The reaction mixture was then allowed to cool to ambient temperature and was added to water. The product was extracted with ethyl acetate and hexane was added to the ethyl acetate phase before washing several times with water and brine. The organic phase was dried, filtered and concentrated to give the title compound as a white solid (0.23 g, 77% yield): ¹H NMR (CDCl₃): δ 7.9 (dd, 1H), 7.23 (dd, 1H), 6.22 (s, 1H), 4.8 (br s, 2H), 2.57 (s, 3H).

12. Preparation of 6-Amino-2-(4-chloro-2,5-difluorophenyl)pyrimidine-4-carboxylic acid methyl ester 2-(4-chloro-2,5-difluorophenyl)-6-methylsulfanylpyrimidin-4-ylamine (0.23 g, 0.8 mmol) was combined in 15 mL chloroform with 77% m-chloroperoxybenzoic acid (0.4 g, 1.78 mmol) and the reaction mixture was stirred overnight. The reaction mixture was concentrated and partitioned between ethyl acetate and an aqueous solution of sodium thiosulfate. The organic phase was washed with aqueous sodium bicarbonate, dried and concentrated. The product was then purified by column chromatography (ethyl acetate/hexane gradient) to give 0.16 g of white solid (63% yield). This intermediate product was then combined in 2 mL DMF with potassium cyanide (0.040 g, 0.6 mmol) and heated at 100° C. for 16 hours. The cooled reaction mixture was partitioned between ethyl acetate and water. The organic phase was washed with brine, diluted with hexane, washed again with water, dried and concentrated to give 0.13 g of a beige solid product (97% yield). This intermediate product was dissolved in 15 mL methanolic HCl generated by added a large excess of acetyl chloride to methanol. The resulting reaction solution was heated at reflux for 8 hours, allowed to cooled to ambient temperature, and diluted with ethyl acetate and water. The organic phase was washed with aqueous sodium bicarbonate, dried and concentrated to give the title compound as a solid (0.090 g, 63% yield): ¹H NMR (CDCl₃): δ 7.9 (dd, 1H), 7.24 (dd, 1H), 7.15 (s, 1H), 5.2 (br s, 2H), 4.0 (s, 3H).

13. Preparation of 6-Amino-5-chloro-2-(4-chloro-2,5-difluorophenyl)-pyrimidine-4-carboxylic acid methyl ester (Compound 20)

6-Amino-2-(4-chloro-2,5-difluorophenyl)pyrimidine-4-carboxylic acid methyl ester (0.090 g, 0.3 mmol) and N-chlorosuccinimide (0.05 g, 0.37 mmol) were combined in 10 mL acetonitrile and heated at 40° C. for 18 hours. The reaction mixture was concentrated and the product purified by column chromatography (ethyl acetate/hexane gradient) to yield the title compound as an off-white solid (0.050 g, 50% yield): ¹H NMR (CDCl₃): δ 7.85 (dd, 1H), 7.22 (dd, 1H), 5.62 (br s, 2H), 4.01 (s, 3H).

14. Preparation of Herbicidal Compositions

In the following illustrative compositions, parts and percentages are by weight.

| EMULSIFIABLE CONCENTRATES | WT % |
|---|---|
| Formulation A | |
| Compound 1 | 26.2 |
| Polyglycol 26-3 | 5.2 |
| Nonionic emulsifier-(di-sec-butyl)-phenyl-poly(oxypropylene)block polymer with (oxyethylene). The polyoxyethelene content is about 12 moles. | |
| Witconate P12-20 (Anionic emulsifier-calcium dodecylbenzene sulfonate-60 wt. % active) | 5.2 |
| Aromatic 100 (Xylene range aromatic solvent) | 63.4 |
| Formulation B | |
| Compound 2 | 3.5 |
| Sunspray 11N (paraffin oil) | 40.0 |
| Polyglycol 26-3 | 19.0 |
| Oleic acid | 1.0 |
| Xylene range aromatic solvent | 36.5 |
| Formulation C | |
| Compound 5 | 13.2 |
| Stepon C-65 | 25.7 |
| Ethomeen T/25 | 7.7 |
| Ethomeen T/15 | 18.0 |
| Xylene range aromatic solvent | 35.4 |
| Formulation D | |
| Compound 19 | 30.0 |
| Agrimer Al-10LC (emulsifier) | 3.0 |
| N-methyl-2-pyrrolidone | 67.0 |
| Formulation E | |
| Compound 5 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

| WETTABLE POWDERS | WT % |
|---|---|
| Formulation F | |
| Compound 12 | 26.0 |
| Polyglycol 26-3 | 2.0 |
| Polyfon H | 4.0 |
| Zeosyl 100 (Precipitated hydrated SiO₂) | 17.0 |
| Barden clay + inerts | 51.0 |
| Formulation G | |
| Compound 14 | 62.4 |
| Polyfon H (sodium salt of lignin sulfonate) | 6.0 |
| Sellogen HR (sodium naphthalene sulfonate) | 4.0 |
| Zeosyl 100 | 27.6 |
| Formulation H | |
| Compound 16 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

| WATER DISPERSIBLE GRANULES Formulation I | |
|---|---|
| | WT % |
| Compound 18 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

| GRANULES Formulation J | |
|---|---|
| | WT % |
| Compound 10 | 5.0 |
| Celetom MP-88 | 95.0 |

The active ingredient is applied in a polar solvent such as N-methylpyrollidinone, cyclohexanone, gamma-butyrolactone, etc. to the Celetom MP 88 carrier or to other suitable carriers. The resulting granules can be applied by hand, granule applicator, airplane, etc. in order to control weeds.

| Formulation K | |
|---|---|
| | WT % |
| Compound 12 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

| WATER SOLUBLE LIQUIDS Formulation L | |
|---|---|
| | WT % |
| Compound 17 | 3.67 |
| Monoethanolamine pH buffer | 0.5 |
| Water | 95.83 |

The active ingredient is dissolved in an appropriate amount of water and the additional monoethanolamine is added as a buffer. A water-soluble surfactant may be added. Other aids may be incorporated to improve physical, chemical and/or formulation properties.

15. Evaluation of General Postemergence Herbicidal Activity

Seeds or nutlets of the desired test plant species were planted in Sun Gro MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hour photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v (volume/volume) mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain 1/2X, 1/4X, 1/8X and 1/16X rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Table 1.

TABLE 1

Post-emergent Weed Control

[Chemical structure: pyrimidine with NH2, Cl, F substituents, phenyl ring with X, Y, Z substituents, and carboxylate ester O-M group]

| | | | | | | % Growth Reduction | | | |
|---|---|---|---|---|---|---|---|---|---|
| Compound | X | Y | Z | M | Rate g ai/ha | ABUTH | POLCO | CIRAR | ECHCG |
| 1 | H | Cl | H | CH₃ | 140 | 100 | 95 | 100 | 90 |
| 2 | F | Cl | H | CH₃ | 140 | 100 | 100 | 100 | 95 |
| 4 | F | CH₃ | H | CH₃ | 140 | 99 | 80 | 60 | 90 |
| 5 | H | CF₃ | H | CH₃ | 140 | 70 | 80 | 85 | 0 |
| 6 | F | CF₃ | H | CH₃ | 140 | 90 | 95 | 80 | 25 |
| 8 | H | CH₃ | F | CH₃ | 140 | 95 | 60 | 45 | 0 |
| 9 | H | CF₂ | H | CH₃ | 140 | 45 | 35 | 40 | 0 |
| 10 | H | Cl | Cl | CH₃ | 140 | 90 | 100 | 95 | ND |
| 11 | H | Cl | H | H | 140 | 99 | 100 | 100 | 85 |
| 12 | F | Cl | H | H | 140 | 100 | 100 | 90 | 90 |
| 14 | F | CH₃ | H | H | 140 | 90 | 80 | 85 | 95 |
| 15 | H | CF₃ | H | H | 140 | 40 | 65 | 80 | 50 |
| 16 | F | CF₃ | H | H | 140 | 65 | 95 | 90 | 90 |
| 17 | H | Cl | Cl | H | 140 | 85 | 95 | 90 | ND |
| 18 | H | CH₃ | F | H | 140 | 100 | 40 | 100 | 75 |
| 19 | H | Cl | H | CH₂CH₃ | 140 | 99 | 100 | 95 | 80 |
| 20 | H | Cl | F | CH₃ | 140 | 99 | 100 | 95 | 95 |

ND = Not determined
ABUTH—Velvetleaf (*Abutilon theophrasti*)
POLCO—Wild buckwheat (*Polygonum convolvulus*)
CIRAR—Canada thistle (*Cirsium arvense*)
ECHCG—Barnyardgrass (*Echinochloa crus-galli*)

16. Evaluation of General Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 25 mL glass vial and was dissolved in 6 mL of a 97:3 v/v (volume/volume) mixture of acetone and DMSO to obtain concentrated stock solutions. If the test compound did not dissolve readily, the mixture was warmed and/or sonicated. The stock solutions obtained were diluted with 18 mL of a 0.1% v/v aqueous solution of Tween® 20 surfactant to obtain spray solutions containing the highest application rate. Additional application rates were obtained by serial dilution of 12 mL of the high rate solution into a solution containing 3 mL of 97:3 v/v mixture of acetone and DMSO and 9 mL of the 0.1% v/v aqueous solution of Tween® 20 surfactant to obtain 1/2X, 1/4X, 1/8X and 1/16X rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 square meters at a spray height of 18 inches (43 cm) above the soil surface. Control plants were sprayed in the same manner with the solvent blank.

The treated pots and control pots were placed in a greenhouse maintained with an approximate 15 hour photoperiod and temperatures of about 23-29° C. during the day and 22-28° C. during the night. Nutrients and water were added on a regular basis and supplemental lighting was provided with overhead metal halide 1000-Watt lamps as necessary. The water was added by top-irrigation. After 20-22 days, the condition of the test plants that germinated and grew as compared with that of the untreated plants that emerged and grew was determined visually and scored on a scale of 0 to 100 percent where 0 corresponds to no injury and 100 corresponds to complete kill or no emergence.

Some of the compounds tested, application rates employed, plant species tested, and results are given in Table 2.

TABLE 2

Pre-emergent Weed Control

| Compound | Rate g ai/ha | % Growth Inhibition | | | | |
|---|---|---|---|---|---|---|
| | | ZEAMX | CHEAL | ABUTH | HELAN | SORVU |
| 11 | 140 | 0 | 100 | 90 | 95 | 95 |
| 12 | 140 | 15 | 100 | 100 | 100 | 90 |
| 13 | 140 | 10 | 95 | 95 | ND | 50 |

TABLE 2-continued

| | | Pre-emergent Weed Control | | | | |
|---|---|---|---|---|---|---|
| Com- | Rate | % Growth Inhibition | | | | |
| pound | g ai/ha | ZEAMX | CHEAL | ABUTH | HELAN | SORVU |
| 14 | 140 | 30 | 100 | 100 | 60 | 40 |
| 15 | 140 | 65 | 60 | 10 | 10 | 0 |
| 16 | 140 | 30 | 100 | 60 | 65 | 60 |

ND = Not determined
ZEAMX - Corn (*Zea mays*)
CHEAL - Common lambsquarters (*Chenopodium album*)
ABUTH - Velvetleaf (*Abutilon theophrasti*)
HELAN - Common sunflower (*Helianthus annuus*)
SORVU - Common sorghum (*Sorghum vulgare*)

What is claimed is:

1. A method of controlling undesirable vegetation in corn which comprises applying to the soil to prevent the emergence of the undesirable vegetation an herbicidally effective amount of a compound of formula I,

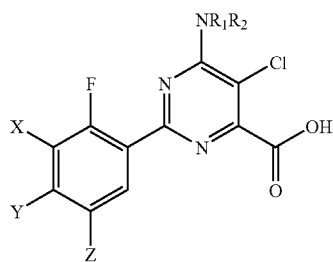

wherein
X represents H or halogen;
Y represents halogen, $C_1$-$C_4$ alkyl or $C_1$-$C_4$ haloalkyl;
Z represents H or halogen, with the proviso that at least one of X or Z is halogen and when Z is halogen then X represents H; and
$R_1$ and $R_2$ independently represent H, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated ring;
and agriculturally acceptable derivatives of the carboxylic acid group.

2. The method of claim 1, wherein the compound of formula I is:
6-amino-5-chloro-2-(4-chloro-2,3-difluorophenyl)pyrimidine-4-caroxylic acid methyl ester 6-amino-5-chloro-2-(2-fluoro-4-methylphenyl)pyrimidine-4-carboxylic acid methyl ester;
6-amino-5-chloro-2-(2,3-difluoro-4-methylphenyl)pyrimidine-4-carboxylic acid methyl ester;
6-amino-5-chloro-2-(2,3-difluoro-4-trifluoromethylphenyl)pyrimidne-4-carboxylic acid;
6-amino-5-chloro-2-(2,5-difluoro-4-methylphenyl)pyrimidine-4-carboxylic acid methyl ester;
6-amino-5-chloro-2-(4,5-dichloro-2-fluorophenyl)pyrimidine-4-carboxylic acid methyl ester;
6-amino-5-chloro-2-(4-chloro-2,3-difluorophenyl)pyrimidine-4-carboxylic acid;
6-amino-5-chloro-2-(2,3-difluoro-4-methylphenyl)pyrimidine-4-carboxylic acid;
6-amino-5-chloro-2-(2,3-difluoro-4-trifluoromethylphenyl)pyrimidine-4-carboxylic acid;
6-amino-5-chloro-2-(4.5-dichloro-2-fluorophenyl)pyrimidine-4-carboxylic acid;
6-amino-5-chloro-2-(2,5-difluoro-4-methylphenyl)pyrimidine-4-carboxylic acid; or 6-amino-5-chloro-2-(4-chloro-2,5-difluorophenyl)-pyrimidine-4-carboxylic acid methyl ester.

3. The method of claim 1, wherein the compound is 6-amino-5-chloro-2-(4-chloro-2,3-difluorophenyl)pyrimidine-4-caroxylic acid methyl ester.

4. The method of claim 1, wherein compound is 6-amino-5-chloro-2-(2-fluoro-4-methylphenyl)pyrimidine-4-carboxylic acid methyl ester.

5. The method of claim 1, wherein the compound is 6-amino-5-chloro-2-(2,3-difluoro-4-methylphenyl)pyrimidine-4-carboxylic acid methyl ester.

6. The method of claim 1, wherein the compound is 6-amino-5-chloro-2-(2,3-difluoro-4-trifluoromethylphenyl)pyirimidne-4-carboxylic acid.

7. The method of claim 1, wherein the compound is 6-amino-5-chloro-2-(2,5-difluoro-4-methylphenyl)pyrimidine-4-carboxylic acid methyl ester.

8. The method of claim 1, wherein the compound is 6-amino-5-chloro-2-(4,5-dichloro-2-fluorophenyl)pyrimidine-4-carboxylic acid methyl ester.

9. The method of claim 1, wherein the compound is 6-amino-5-chloro-2-(4-chloro-2,3-difluorophenyl)pyrimidine-4-carboxylic acid.

10. The method of claim 1, wherein the compound is 6-amino-5-chloro-2-(2,3-difluoro-4-methylphenyl)pyrimidine-4-carboxylic acid.

11. The method of claim 1, wherein the compound is 6-amino-5-chloro-2-(2,3-difluoro-4-trifluoromethylphenyl)pyrimidine-4-carboxylic acid.

12. The method of claim 1, wherein the compound is 6-amino-5-chloro-2-(4.5-dichloro-2-fluorophenyl)pyrimidine-4-carboxylic acid.

13. The method of claim 1, wherein the compound is 6-amino-5-chloro-2-(2,5-difluoro-4-methylphenyl)pyrimidine-4-carboxylic acid.

14. The method of claim 1, wherein the compound is 6-amino-5-chloro-2-(4-chloro-2,5-difluorophenyl)-pyrimidine-4-carboxylic acid methyl ester.

* * * * *